US011291780B2

United States Patent
Porteous (10) Patent No.: US 11,291,780 B2
(45) Date of Patent: Apr. 5, 2022

(54) BREATH-ACTUATED NEBULIZER FOR MEDICINE INHALATION

(71) Applicant: CareFusion 2200, Inc., San Diego, CA (US)

(72) Inventor: Eric Porteous, Corona, CA (US)

(73) Assignee: Vyaire Medical Consumables LLC, Yorba Linda, CA (US)

( * ) Notice: Subject to any disclaimer, the term of this patent is extended or adjusted under 35 U.S.C. 154(b) by 1418 days.

(21) Appl. No.: 14/957,449

(22) Filed: Dec. 2, 2015

(65) Prior Publication Data
US 2016/0158467 A1 Jun. 9, 2016

Related U.S. Application Data

(60) Provisional application No. 62/087,730, filed on Dec. 4, 2014.

(51) Int. Cl.
  *A61M 11/02* (2006.01)
  *A61M 15/00* (2006.01)
  *A61M 11/06* (2006.01)

(52) U.S. Cl.
  CPC ............. *A61M 11/02* (2013.01); *A61M 11/06* (2013.01); *A61M 15/002* (2014.02); *A61M 2205/8225* (2013.01)

(58) Field of Classification Search
  CPC .......... A61M 16/0069; A61M 2230/40; A61M 2230/005; A61M 2202/0007;
  (Continued)

(56) References Cited

U.S. PATENT DOCUMENTS 3,580,249 A * 5/1971 Takaoka ............... A61M 16/125
                                                           128/200.14
3,658,059 A    4/1972 Steil
(Continued)

FOREIGN PATENT DOCUMENTS

CN     2298817 Y    12/1998
CN     101141992 A   3/2008
(Continued)

OTHER PUBLICATIONS

"Venturi Definition—Merriam Webster" (Year: 2021).*
(Continued)

*Primary Examiner* — Timothy A Stanis
*Assistant Examiner* — Benjamin M. Kusiak
(74) *Attorney, Agent, or Firm* — Morgan, Lewis & Bockius LLP (57) ABSTRACT

Breath-actuated nebulizers for delivering medicine are provided, including an outlet port; an opening; and a medicine cup coupled to the opening through a venturi tube. The medicine cup receives a medicine to be delivered through the outlet port, and is coupled to the outlet port. Some embodiments include a jet nozzle coupled to a pressurized gas source and protruding into the medicine cup, and a sleeve in the medicine cup fluidically coupling the venturi tube to the medicine cup and forming a capillary volume with the jet nozzle. In some embodiments, a rib supports a diverter disposed above a nozzle tip to form a radial flow of the pressurized gas away from a nozzle axis. Also provided is a method for manufacturing and using the above nebulizer.

11 Claims, 6 Drawing Sheets

(58) Field of Classification Search
CPC ...... A61M 2202/0208; A61M 2230/42; A61M 16/0045; A61M 16/0057; A61M 16/024; A61M 16/026; A61M 16/06; A61M 16/0666; A61M 16/12; A61M 16/16; A61M 2016/0027; A61M 2016/0033; A61M 2205/3334; A61M 2205/3365; A61M 2205/3375; A61M 2205/50
See application file for complete search history.

(56) References Cited

U.S. PATENT DOCUMENTS

| | | | |
|---|---|---|---|
| 4,512,341 A | 4/1985 | Lester | |
| 4,566,451 A * | 1/1986 | Badewien | A61M 15/00 128/200.21 |
| 4,657,007 A * | 4/1987 | Carlin | A61M 11/06 128/200.18 |
| 4,746,067 A * | 5/1988 | Svoboda | A61M 11/06 239/338 |
| 5,209,225 A * | 5/1993 | Glenn | A61M 11/06 128/200.14 |
| 5,259,370 A * | 11/1993 | Howe | A61M 16/16 128/200.14 |
| 5,508,269 A * | 4/1996 | Smith | A61K 9/0078 514/38 |
| 5,584,285 A * | 12/1996 | Salter | A61M 11/06 128/200.21 |
| 6,044,841 A * | 4/2000 | Verdun | A61M 11/06 128/200.18 |
| 6,085,741 A * | 7/2000 | Becker | A61M 11/06 128/200.14 |
| 6,129,080 A * | 10/2000 | Pitcher | A61M 11/06 128/200.21 |
| 6,237,589 B1 * | 5/2001 | Denyer | A61M 11/06 128/200.21 |
| 6,338,443 B1 * | 1/2002 | Piper | A61M 11/06 128/200.18 |
| 6,450,163 B1 | 9/2002 | Blacker et al. | |
| 6,929,003 B2 * | 8/2005 | Blacker | A61M 11/06 128/203.12 |
| 7,267,120 B2 * | 9/2007 | Rustad | A61M 11/00 128/200.18 |
| 7,568,480 B2 * | 8/2009 | Foley | A61M 11/06 128/200.14 |
| 7,841,336 B2 * | 11/2010 | Rivera | A61M 15/0091 128/200.21 |
| 7,954,487 B2 * | 6/2011 | Grychowski | A61M 11/06 128/200.14 |
| 8,061,352 B2 * | 11/2011 | Grychowski | A61M 11/06 128/200.14 |
| 8,397,712 B2 * | 3/2013 | Foley | A61M 11/06 128/200.14 |
| 8,596,263 B2 * | 12/2013 | Piper | A61M 11/06 128/200.14 |
| 8,671,934 B2 | 3/2014 | Addington et al. | |
| 8,844,520 B2 * | 9/2014 | Foley | A61M 11/06 128/200.14 |
| 9,022,023 B2 * | 5/2015 | Korneff | A61M 11/007 128/200.21 |
| 9,227,030 B2 * | 1/2016 | Stedman | B01F 5/0428 |
| 9,364,618 B2 * | 6/2016 | Blacker | A61M 11/06 |
| 9,539,408 B2 * | 1/2017 | Pevler | A61M 11/06 |
| 9,757,528 B2 * | 9/2017 | Rubin | A61M 11/02 |
| 10,668,229 B2 * | 6/2020 | Pevler | A61M 11/02 |
| 2002/0020762 A1 * | 2/2002 | Selzer | A61M 11/06 239/390 |
| 2002/0112720 A1 * | 8/2002 | Abate | A61M 11/06 128/200.21 |
| 2003/0181917 A1 * | 9/2003 | Gertner | B05B 7/2443 606/82 |
| 2003/0192962 A1 * | 10/2003 | Fraccaroli | A61M 11/002 239/338 |
| 2004/0031485 A1 * | 2/2004 | Rustad | A61M 11/06 128/200.18 |
| 2007/0227535 A1 * | 10/2007 | Harrington | A61M 15/0096 128/200.21 |
| 2007/0227536 A1 * | 10/2007 | Rivera | B05B 7/0012 128/200.21 |
| 2009/0126734 A1 * | 5/2009 | Dunsmore | A61M 16/0858 128/203.25 |
| 2010/0147292 A1 * | 6/2010 | Hamaguchi | A61M 11/06 128/200.23 |
| 2010/0204602 A1 | 8/2010 | Addington et al. | |
| 2011/0100360 A1 * | 5/2011 | Faram | A61M 16/021 128/200.23 |
| 2011/0155129 A1 * | 6/2011 | Stedman | F04F 5/463 128/200.23 |
| 2011/0168169 A1 * | 7/2011 | Blacker | A61M 11/06 128/200.14 |
| 2012/0000461 A1 * | 1/2012 | Grychowski | A61M 11/06 128/200.21 |
| 2013/0074842 A1 * | 3/2013 | Boucher | A61P 11/06 128/203.16 |
| 2013/0247903 A1 * | 9/2013 | Foley | A61M 11/06 128/200.21 |
| 2013/0327323 A1 * | 12/2013 | Rubin | A61M 16/1055 128/200.18 |
| 2013/0333695 A1 * | 12/2013 | Dellaca | A61M 15/0091 128/200.14 |
| 2014/0224247 A1 * | 8/2014 | Tan | A61M 16/14 128/203.14 |
| 2014/0290646 A1 * | 10/2014 | Koehler | A61M 11/001 128/200.14 |
| 2016/0106947 A1 * | 4/2016 | Flynn | A61M 16/06 128/200.14 |
| 2016/0228670 A1 * | 8/2016 | Av-Gay | A61M 16/0057 |
| 2016/0303336 A1 * | 10/2016 | Arp | A61K 31/167 |
| 2017/0007781 A1 * | 1/2017 | Blacker | A61M 11/06 |
| 2018/0008789 A1 * | 1/2018 | Alizoti | A61M 15/0093 |
| 2018/0161531 A1 * | 6/2018 | Costella | A61M 15/0021 |

FOREIGN PATENT DOCUMENTS

| | | |
|---|---|---|
| CN | 101151025 A | 3/2008 |
| CN | 101277731 A | 10/2008 |
| CN | 201710772 U | 1/2011 |
| CN | 201862090 U | 6/2011 |
| CN | 102470226 A | 5/2012 |
| CN | 103157161 A | 6/2013 |
| CN | 103180053 A | 6/2013 |
| EP | 0653218 A1 | 5/1995 |
| EP | 2005981 B1 | 9/2012 |

OTHER PUBLICATIONS

International Search Report and Written Opinion for Application No. PCT/US2015/063400, dated Feb. 19, 2016, 17 pages.
Chinese Office Action for Application No. 201510884524.6, dated Sep. 30, 2019, 19 pages.
Chinese Office Action for Application No. 201510884524.6, dated Mar. 24, 2020, 6 pages.
Chinese Office Action for Application No. 201510884524.6, dated Jun. 10, 2020, 32 pages.
Chinese Office Action for Application No. 201510884524.6, dated Dec. 23, 2020, 39 pages including English translation.

* cited by examiner

602 — Remove cap from a medicine cup in a nebulizer

604 — Provide medication to the medicine cup

606 — Adjust a sleeve supporting a venturi tube on a jet nozzle to form a capillary volume 608 — Couple nebulizer to pressurized gas source 610 — Couple outlet port in the nebulizer to a patient respiratory channel

FIG. 6

BREATH-ACTUATED NEBULIZER FOR MEDICINE INHALATION

CROSS REFERENCE TO RELATED APPLICATIONS

The following application claims priority to U.S. Provisional Patent Application No. 62/087,730 entitled BREATH-ACTUATED NEBULIZER FOR MEDICINE INHALATION, filed on Dec. 4, 2014, the contents of which are herein incorporated by reference in their entirety, for all purposes.

BACKGROUND

Field

The present disclosure is related to an apparatus and method for generating an aerosol for delivery to a patient. More particularly, the present disclosure is related to a breath-actuated nebulizer configured to generate an aerosol in coordination with a patient's breathing.

Description of Related Art

Nebulizers for providing aerosolized medicine to a patient are commonly used in the healthcare industry. In many instances, it is desirable that the nebulizer provides automatic delivery to the patient, as the patient inhales. Some nebulizers deliver medication to the patient only when the patient inhales, reducing or ceasing delivery of medication when the patient is not breathing or when the patient exhales. These nebulizers provide a higher certainty that the patient actually received the intended medication.

SUMMARY

Described herein are embodiments of breath-actuated nebulizers that deliver medication to a patient when the patient inhales and reducing or ceases delivery of medication to the patient when the patient is not breathing or when the patient exhales. The breath-actuated feature of the nebulizers reduces the exposure of caregivers to aerosolized medication otherwise prevalent in many continuous nebulizers. Some nebulizers that automatically cease medicine delivery include moving components that adapt to pressure and volume variations produced by the patient's breathing. The devices are configured so the moving components, which include membranes and deformable pieces made of resilient materials, actuate a nebulizing mechanism that provides aerosolized medicine to the patient. A drawback of such devices is a reduced reliability due to wear of the moving components. Another problem typically encountered with moving components is the longer response time associated with mechanical motion. Also, use of adequate resilient materials is expensive and imposes certain requirements for the rigid components of the device. For example, attaching a moving membrane to a rigid plastic piece imposes restrictions on the materials and method of fabrication that are difficult to implement on a mass production configuration.

Some embodiments described herein include a breath-actuated nebulizer for delivering medicine, comprising: a medicine cup configured to hold medicine and comprising (i) an ambient gas inlet configured to permit ambient gas into the medicine cup, (ii) a pressurized gas inlet configured to conduct pressurized gas into the medicine cup, and (iii) an outlet configured to direct gas out of the medicine cup; a venturi passage comprising a throat, the passage being configured to conduct the ambient gas from the inlet to within the medicine cup; a jet nozzle configured to receive the pressurized gas and comprising a jet orifice configured to produce a jet stream of the pressurized gas within the medicine cup; and a pressure passage comprising (i) a first portion comprising a venturi hole that provides fluid communication with the venturi passage throat, (ii) a second portion comprising a medicine inlet that provides fluid communication with the medicine cup, and (iii) a third portion, between the first and second portions, comprising a conducting opening that is configured to conduct medicine from the second portion toward the jet stream; wherein when ambient gas is drawn into the medicine cup through the venturi passage, a pressure within the pressure passage is reduced such that medicine is drawn up through the second portion until the medicine is conducted to the jet stream via the conducting opening.

In some embodiments, a breath-actuated nebulizer for delivering medicine is provided, including: a medicine cup configured to hold medicine and comprising (i) a first gas inlet, (ii) a second gas inlet configured to conduct pressurized gas into the medicine cup, and (iii) an outlet that directs gas out of the medicine cup; a jet nozzle, in fluid communication with the second gas inlet, comprising a jet orifice configured to produce a jet stream of the pressurized gas; a venturi passage comprising a throat in fluid communication with the first gas inlet and, via a passage, the medicine cup; wherein, without moving parts of the nebulizer, the passage changes from a first high pressure, when gas is not drawn into the medicine cup through the venturi passage and medicine is not conducted from the medicine cup through the venturi passage, to a second low pressure, when gas is drawn into the medicine cup through the venturi passage and medicine is conducted from the medicine cup toward the jet stream.

In some embodiments, a breath-actuated nebulizer for delivering medicine includes an outlet port, an opening, and a medicine cup coupled to the opening through a venturi tube. The medicine cup is configured to receive a medicine to be delivered through the outlet port, and is fluidically coupled to the outlet port. The nebulizer further includes a jet nozzle configured to be coupled to a pressurized gas source and to deliver the pressurized gas into the medicine cup, a sleeve in the medicine cup, the sleeve fluidically coupling the venturi tube to the medicine cup and forming a capillary volume with the jet nozzle, and a rib formed on the sleeve and supporting a diverter disposed above a nozzle tip. The diverter is configured to form a radial flow of the pressurized gas away from a nozzle axis.

Some methods include forming a medicine cup having an upper chamber and a lower chamber coupled by a fluid channel, and forming an outlet port on a cap that fits the medicine cup. The method further includes forming a sleeve that fits onto a jet nozzle, slide fitting the sleeve onto the jet nozzle in the medicine cup, welding together a venturi tube and the sleeve; and assembling the cap to the sleeve and the venturi.

Some methods provided herein include removing a cap from a medicine cup in a nebulizer; providing medicine to the medicine cup; and coupling the nebulizer to a pressurized gas source such that a jet stream is created; wherein, without moving parts of the nebulizer, the nebulizer switches from a first state, when gas is being evacuated from the medicine cup and medicine is drawn from the medicine cup toward the jet stream, to a second state, when gas is not evacuated from the medicine cup and medicine is not drawn from the medicine cup toward the jet stream.

Some methods include removing a cap from a medicine cup in a nebulizer, providing medicine to the medicine cup, adjusting a sleeve supporting a venturi tube on a jet nozzle, coupling the nebulizer to a pressurized gas source, and coupling an outlet port in the nebulizer to a patient's respiratory channel.

DETAILED DESCRIPTION

In healthcare facilities it is often desired to deliver aerosolized medication to patients through respiratory channels. This is typically done with nebulizers that are continuously running units. It is desirable to provide a nebulizer that operates automatically, even when patients are unconscious, semi-conscious, or otherwise unable to actuate the device. Such a device would deliver aerosol only while a patient inhales, thereby ensuring that the patient receives the medication. Also, a breath actuated device reduces substantially the exposure of a caregiver to "second hand" aerosolized medications. Some breath actuated nebulizers currently available include mechanical actuators having moving parts. However, it is desirable that these devices have few or no moving parts so they are inexpensive, easily manufactured on a large scale, and durable. Some embodiments disclosed herein include a breath-actuated nebulizer with no moving parts. The patient's inhalation is directed through a venturi tube, generating a vacuum, or low pressure, that is used directly to pull medicine into a nebulizing position near a jet nozzle tip inside the device. As used herein, the term vacuum is a broad term, and is meant to refer to, among other things, a reduced pressure zone when compared with ambient pressure or a pressure in an area surrounding the reduced pressure zone.

Some embodiments include a venturi tube configured such that one end of the venturi tube is open to ambient air (at about atmospheric pressure), and the opposite end of the venturi tube is fluidically coupled to an outlet port, which can be coupled to an artificial airway of a breathing patient or can be accessed directly by a patient. The venturi tube has a region of reduced diameter ('pinched' region, or 'throat') that accelerates flow, thus generating a vacuum or a relatively low pressure. A port, aperture, hole, or passageway at the venturi throat is fluidically coupled to a reservoir of liquid medication. Accordingly, the vacuum or low pressure generated by the venturi tube is used to draw or pull medication upward, beyond its resting position. Some embodiments include a nozzle assembly including a jet orifice to direct a constant stream of gas from a pressurized gas source (compressed air or oxygen) to flow against a diverting surface or pin. The diverting surface causes a radial wall jet flowing out of an axis defined by the jet nozzle. The radial wall jet flows over a capillary volume at a high speed. This radial wall jet generates a continuous vacuum or low pressure within the capillary volume. The radial wall jet also impinges upon medicine emerging from the capillary volume and aerosolizes or atomizes the medicine in preparation for the medicine to exit the outlet or outlet port in an aerosolized form.

In some embodiments, the capillary volume is fluidically coupled, or "teed," to a medicine tube and to the venturi throat 103, through a nozzle feed tube or conduit. The assembly is configured in such a way that when no patient inhalation occurs, the medicine drains at a distance from the nozzle feed tube, thus preventing the medicine to be drawn into the capillary volume to be aerosolized by the radial wall jet. When a patient inhales, or when gas is drawn from the medicine cup through the outlet, the vacuum, or pressure drop, generated by the venturi tube pulls the medicine into proximity of the nozzle feed tube, and the radial wall jet draws the liquid medicine out of the capillary volume to be aerosolized in the radial jet stream. Accordingly, embodiments consistent with the present disclosure provide a mechanism to bring a liquid medication up to a nebulizing position within the device using fluidic forces rather than mechanically actuated moving parts.

Figure 1:
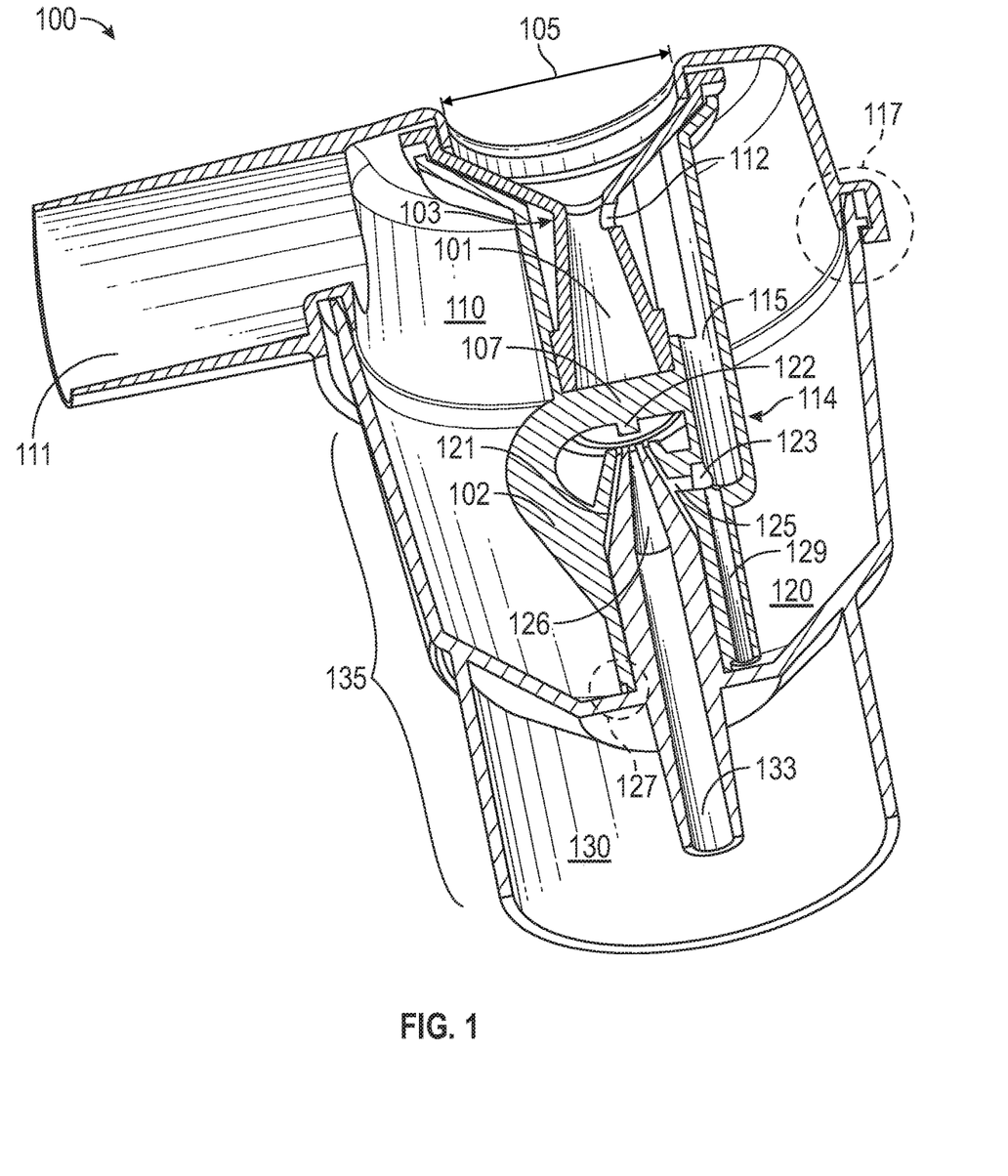
FIG. 1 illustrates a perspective view of a cross section of a breath-actuated nebulizer, according to some embodiments.

FIG. 1 illustrates a perspective view of a cross section of a breath-actuated nebulizer 100, according to some embodiments. Breath-actuated nebulizer 100 for delivering medicine can include an outlet port 111; an opening 105, and a medicine cup 135 coupled to opening 105 through a venturi tube 101. Outlet port 111 protrudes from a cap 110 that snap fits to an upper chamber 120 of medicine cup 135, by pressure. Some embodiments may optionally include a mouth piece that couples the patient's mouth to outlet port 111. Further according to some embodiments, outlet port 111 may be configured to attach to a mask that fits onto the patient's face, fixing outlet port 111 relative to the patient's respiratory channels. In some embodiments, cap 110 is secured to medicine cup 135 through tongue 117. Accordingly, tongue 117 may be configured as a quarter turn fastener. Further according to some embodiments, cap 110 may be secured to medicine cup 135 by threads formed on the inside of cap 110 and the outside of the rim in upper chamber 120. Upper chamber 120 is configured to receive liquid medicine and is separated by a jet nozzle 126 from a bottom chamber 130. Bottom chamber 130 is coupled to the pressurized gas source through a pressurized gas port 133.

Medicine cup 135 is fluidically coupled to outlet port 111. Jet nozzle 126 is configured to be coupled to a pressurized gas source (not shown) and, in the illustrated embodiments, protrudes into medicine cup 135. A sleeve 102 fluidically couples venturi tube 101 to medicine cup 135. In some embodiments, sleeve 102 is pressure fit onto jet nozzle 126 and forms a capillary volume 121 with jet nozzle 126. Capillary volume 121 is formed between the tip of nozzle 126 and sleeve 102. Accordingly, in some embodiments capillary volume 121 is a conical passageway for the liquid medicine. In some embodiments, capillary volume 121 is a frusto-conical passageway for the liquid medicine.

A rib 107 formed on sleeve 102 supports a diverter 122 disposed above the tip or orifice of the jet nozzle 126. Diverter 122, which can be a cylindrical member having a generally flat surface that faces the jet nozzle 126, is configured to form a radial flow of the pressurized gas away from a nozzle axis. Sleeve 102 comprises a pressure passage 114 that includes a vent tube 115. Vent tube 115 is coupled to a throat of venturi tube 101 through a first hole 112, or a venturi hole, having a first diameter. Vent tube 115 is coupled to capillary volume 121 through a second hole 123, or conducting opening, of the pressure passage 114 having a second diameter and a nozzle feed tube 125. The diameter of first hole 112 and the diameter of second hole 123 are selected such that a patient breath pulls the medicine up to the level of second hole 123, where the medicine fluidically contacts nozzle feed tube 125. In some embodiments, nozzle feed tube 125 is generally horizontal. The jet nozzle flow pulls the medicine through capillary volume 121 and into the radially outward gas flow. Sleeve 102 includes a lip 127 coupled to a bottom portion of the upper chamber 120 in medicine cup 135 to hermetically seal capillary volume 121 from medicine cup 135. Lip 127 forms a gap fluidically coupling medicine cup 135 to vent tube 115. In some embodiments, the pressure passage 114 of the sleeve 102 includes a medicine tube 129 fluidically coupling vent tube 115 to medicine cup 135.

When a patient inhales through the outlet, or outlet port 111, or when gas is drawn through the outlet port or outlet, a vacuum, or low pressure zone, is formed in vent tube 115 and medicine is pulled up from the bottom of upper chamber 120 through medicine tube 129. The liquid medicine is aerosolized into small particles that flow through the outlet or outlet port 111 into the patient's respiratory channel by the radial gas flow or jet formed at the tip of jet nozzle 126 after the flow of pressurized gas from the nozzle encounters diverter 122. In some embodiments, the pressurized gas source runs continuously through jet nozzle 126, creating a vacuum in capillary volume 121. Nozzle feed tube 125 runs across to capillary volume 121 at the junction of vent tube 115 and medicine tube 129. Medicine is raised high enough by the patient created vacuum in vent tube 115 to reach nozzle feed tube 125. In operation, when a patient created vacuum is formed in vent tube 115, medicine is prevented to flow up to venturi tube 101 by the vacuum created by jet nozzle 126 in capillary volume 121. In some embodiments, inadvertently actuating the medicine nebulizer by tilting the container may be prevented by the air pressure in vent tube 115 when the patient is not breathing through outlet port 111. Accordingly, nebulizing actuation in breath-actuated nebulizer 100 is 'binary' (on/off) based on patient respiration or the action of drawing gas through the venturi tube or passageway.

A thin rib 107 in sleeve 102 supports diverter 122. Diverter 122 may be a cylinder just above the jet orifice in jet nozzle 126. Accordingly, pressurized gas from jet nozzle 126 impinges on diverter 122 and spreads radially outward, relative to the axis of jet nozzle 126. Medicine is atomized at the nozzle by the high velocity air flowing radially out. Liquid medicine is "sheared off" by the radial flow created between nozzle tip and diverter. Diverter 122 may be flat or have an angle, or a semi-circular dome to change the angle of the spray coming out of the nozzle. Different designs of a specific shape of diverter 122 may be used to increase output. In some embodiments, capillary volume 121 forms a concentric gap around the jet orifice of jet nozzle 126. Accordingly, the pressurized gas exiting jet nozzle 126 hits diverter 122 first and then engage the fluid out of capillary volume 121. In some embodiments, diverter 122 is fixed relative to jet nozzle 126, and there is no need to move the diverter in and out of position to actuate the medicine nebulizer. According to some embodiments, capillary volume 121 is a medicine pathway forming a 0.010" gap between sleeve 102 and jet nozzle 126. Lip 127 at the end of sleeve 102 interferes with a chamfer at the bottom of upper chamber 120 forming a liquid tight seal to avoid medicine leaks into capillary volume 121 from medicine cup 135.

In embodiments consistent with the present disclosure, parts and components in a breath-actuated nebulizer as disclosed herein are fixed with respect to one another in a relatively rigid configuration. Embodiments consistent with the present disclosure include carefully adjusted diameters of first hole 112 and of second hole 123, so as to form a vacuum in capillary volume 121 that brings the medicine from nozzle feed tube 125 in contact with the radial flow generated by jet nozzle 126 and diverter 122. Accordingly, the vacuum in capillary volume 121 created by the radial jet flow is not too high to automatically pull medicine from medicine cup 135, without patient respiration.

Figure 2:
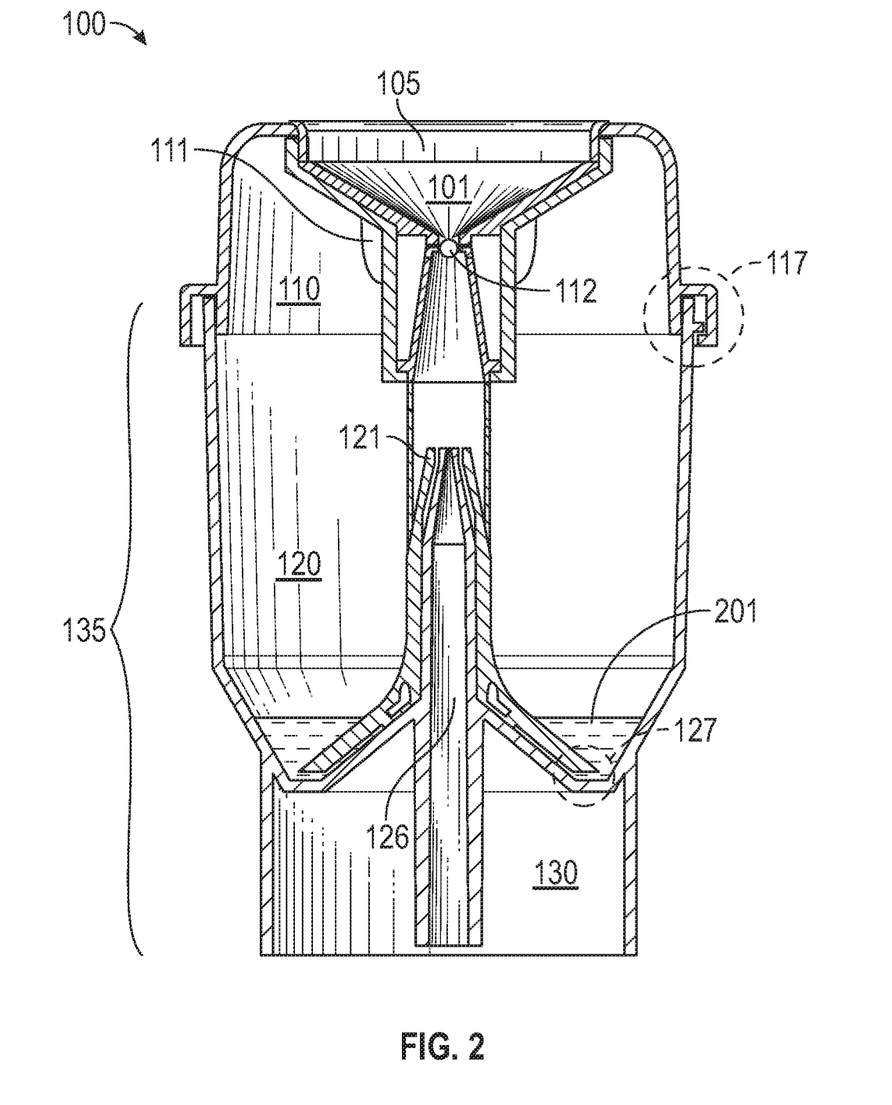
FIG. 2 illustrates a cross section of a breath-actuated nebulizer, according to some embodiments.

FIG. 2 illustrates a cross section of breath-actuated nebulizer 100, according to some embodiments. In that regard, FIG. 2 illustrates a cross-sectional view of breath-actuated nebulizer 100 looking from the side opposite outlet port 111. Elements in FIG. 2 having the same numeral reference as an element in FIG. 1 are the same in both figures, and therefore their description will not be repeated here, unless otherwise indicated. Medicine 201 sits in the bottom of upper chamber 120 waiting for the next patient breath to occur. In some embodiments, outlet port 111, sleeve 102, venturi tube 101, medicine cup 135, and jet nozzle 125 are formed of a rigid material such as plastic. For example, medicine cup 135, venturi tube 101, and sleeve 102 may all be made by injection molded plastic. The breath-actuated nebulizer 100 can include a rib that supports a diverter above and in close proximity to the tip of jet nozzle 126. Also, FIG. 2 shows that, in some embodiments, pressurized gas coming from jet nozzle 126 may exit nebulizer 100 through outlet port 111 and also through venturi tube 101 when the patient is not inhaling.

Figure 3:
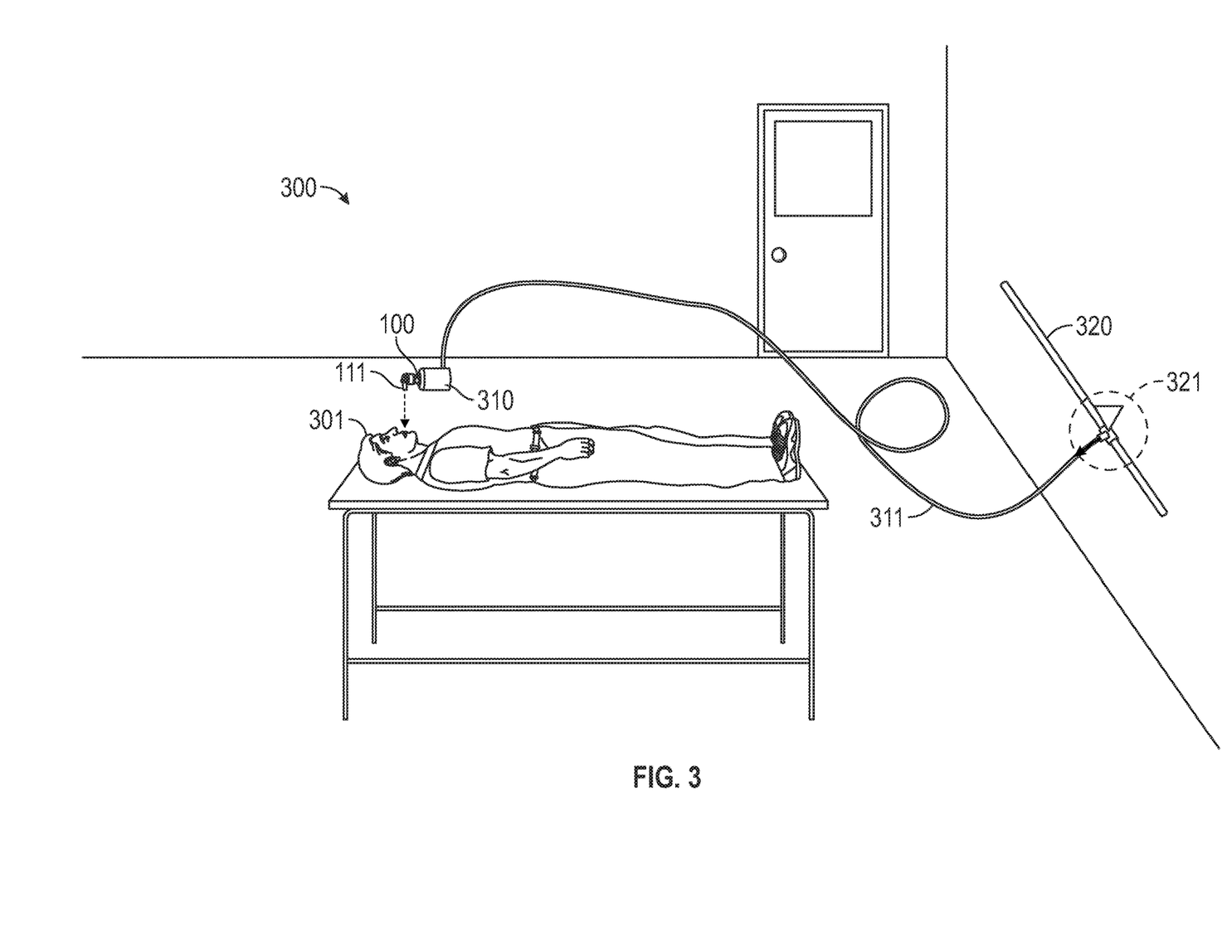
FIG. 3 illustrates a breath-actuated nebulizer used in a healthcare facility, according to some embodiments.

FIG. 3 illustrates a breath-actuated nebulizer 100 used in a healthcare facility 300, according to some embodiments. Accordingly, the pressurized gas source coupled to breath-actuated nebulizer 100 may be a canister 310 containing pressurized gas. In some embodiments, the pressurized gas source is a hose 311 coupled to a gas pipeline 320 running on the wall of healthcare facility 300, through an outlet 321.

Gases used in canister 310 or in hose 311 may include air, oxygen, nitrogen, or any other gas used in healthcare facility 300 in connection with a patient's care. In some embodiments, the gases may include inert gases such as argon (Ar) or helium (He), or other gases such as $CO_2$, and the like. Further, in some embodiments healthcare facility 300 is a surgical room, and breath-actuated nebulizer 100 is used to deliver an anesthetic drug to patient 301. In that regard, the pressurized gas provided by canister 310 or by hose 311 may be an anesthetic component.

Figure 4:
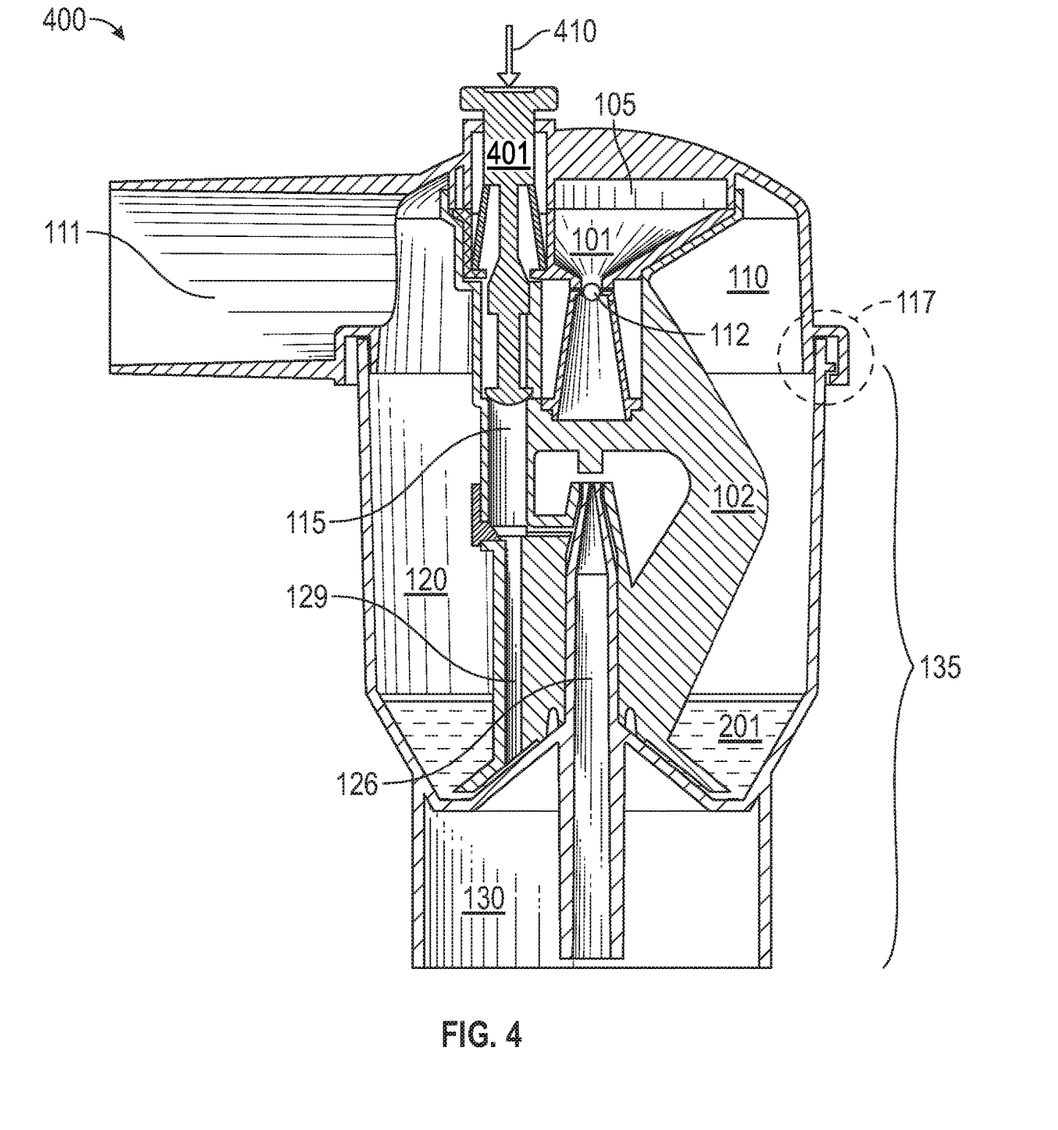
FIG. 4 illustrates a cross section of a breath-actuated nebulizer, according to some embodiments.

FIG. 4 illustrates a cross section of a breath-actuated nebulizer 400, according to some embodiments. Elements of nebulizer 400 that are common to elements of nebulizer 100 have the same numeral reference and are described in detail above (cf. FIG. 1). Therefore, the description of the common elements between nebulizer 400 and nebulizer 100 will not be repeated here, unless otherwise indicated. Nebulizer 400 further comprises a manual override including a push button 401 to actuate a medicine dispenser, bypassing venturi tube 101. Nebulizer 400 including a manual override may be desirable for use with frail or weak patients that are unable to actuate the nebulizer via their own breath. In such configurations, a manual override provided by push button 401 and actuated by either the patient or healthcare personnel activating nebulizer 400 by manually creating a vacuum in vent tube 115, at a desired time. The vacuum is created when a force is applied in the direction of arrow 410, as illustrated.

Figure 5:
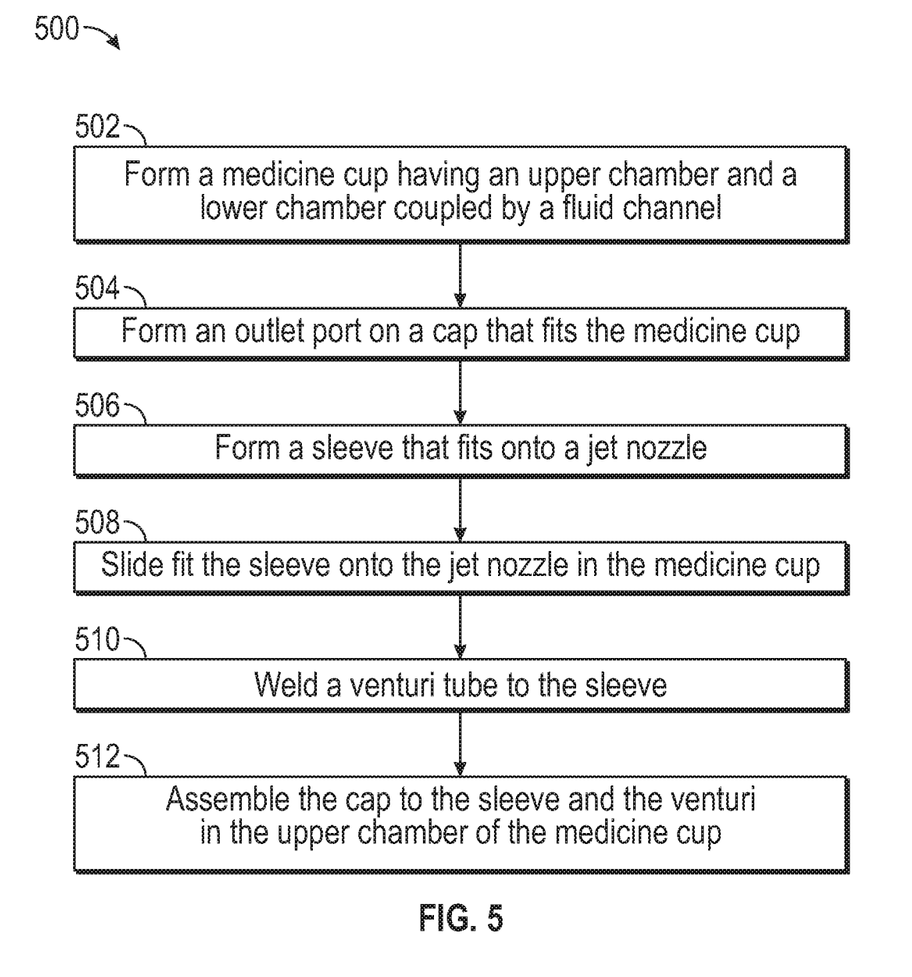
FIG. 5 illustrates a flowchart in a method for assembling a breath-actuated nebulizer, according to some embodiments.

FIG. 5 illustrates a flowchart in a method 500 for assembling a breath-actuated nebulizer, according to some embodiments. Steps in FIG. 5 may be performed at least partially by an automated machine having a computer including a memory circuit and a processor circuit. The memory circuit may store commands which, when executed by the processor circuit, cause the machine to perform the steps in method 500. Steps in methods consistent with method 500 may be performed in any order, and the sequence illustrated in FIG. 5 is not limiting of embodiments consistent with the scope of the present disclosure. Further, some steps in method 500 may be performed overlapping in time. Moreover, some steps in method 500 may be performed simultaneously, or quasi-simultaneously, without departing from the scope of the present disclosure. Methods consistent with the present disclosure may include at least one, but not all of the steps in method 500.

Step 502 includes forming a medicine cup having an upper chamber and a lower chamber coupled by a fluid channel. The medicine cup, the upper chamber, and the lower chamber may be as described in detail above (e.g., medicine cup 135, upper chamber 120 and lower chamber 130, cf. FIG. 1). In some embodiments, step 502 may include forming a jet nozzle on a side of the fluid channel protruding into the upper chamber; and forming a pressurized gas port on a side of the fluid channel protruding into the lower chamber (e.g., jet nozzle 126 and pressurized gas port 133, cf. FIG. 1).

Step 504 includes forming an outlet port on a cap that fits the medicine cup. The outlet port and the cap may be as described in detail above (e.g., outlet port 111 and cap 110, cf. FIG. 1). In some embodiments, the outlet port may be configured to directly enter the mouth of a patient. In some embodiments, the outlet port is configured to couple with a device that enters the mouth of the patient, such as an artificial airway.

Step 506 includes forming a sleeve that fits onto a jet nozzle. The sleeve and the jet nozzle may be as described in detail above (e.g., sleeve 102 and jet nozzle 126, cf. FIG. 1). Step 506 may include forming a rib over the tip of the nozzle in the sleeve, the rib supporting a diverter over the tip of the nozzle (e.g., rib 107 and diverter 122, cf. FIG. 1). Step 508 includes slide fitting the sleeve onto the jet nozzle in the medicine cup. In some embodiments, step 508 may include pressure fitting the sleeve onto the jet nozzle in the medicine cup. In some embodiments, step 508 may include forming a capillary volume between the sleeve and the jet nozzle (e.g., capillary volume 121, FIG. 1). Moreover, in some embodiments step 508 may include hermetically sealing the capillary volume from the upper chamber, except for a small gap coupling a medicine tube in the sleeve to the upper chamber (e.g., medicine tube 129, cf. FIG. 1). In some embodiments, step 508 includes forming a lip on the sleeve that contacts the upper chamber (e.g., lip 127, cf. FIG. 1).

Step 510 includes welding together a venturi tube and the sleeve. In some embodiments, step 510 may include pressure fitting the venturi tube onto the sleeve. The venturi tube may be as described in detail above (e.g., venturi tube 101, cf. FIG. 1). Step 510 may include aligning a hole in the throat of the venturi tube with an opening of a vent tube in the sleeve (e.g., hole 112 and vent tube 115, cf. FIG. 1).

Step 512 includes assembling the cap to the sleeve and the venturi in the upper chamber of the medicine cup. In some embodiments, step 512 may include permanently assembling the cap to the sleeve and the venturi. In some embodiments, step 512 may include snap fitting the cap onto the upper chamber in the medicine cap. The cap has a rim forming the opening, the rim is pressure fit onto an inlet of the venturi tube. Step 512 may include coupling an assembly including the cap, the sleeve, the venturi tube and the medicine cup onto a pressurized gas source. In some embodiments, step 512 includes turning the cap around the medicine cup. For example, in some embodiments step 512 may include making a ¼ turn so that a tongue fixes the cap onto the medicine cup (e.g., tongue 117, cf. FIG. 1). In some embodiments, step 512 may include threading the cap onto the medicine cup.

Figure 6:
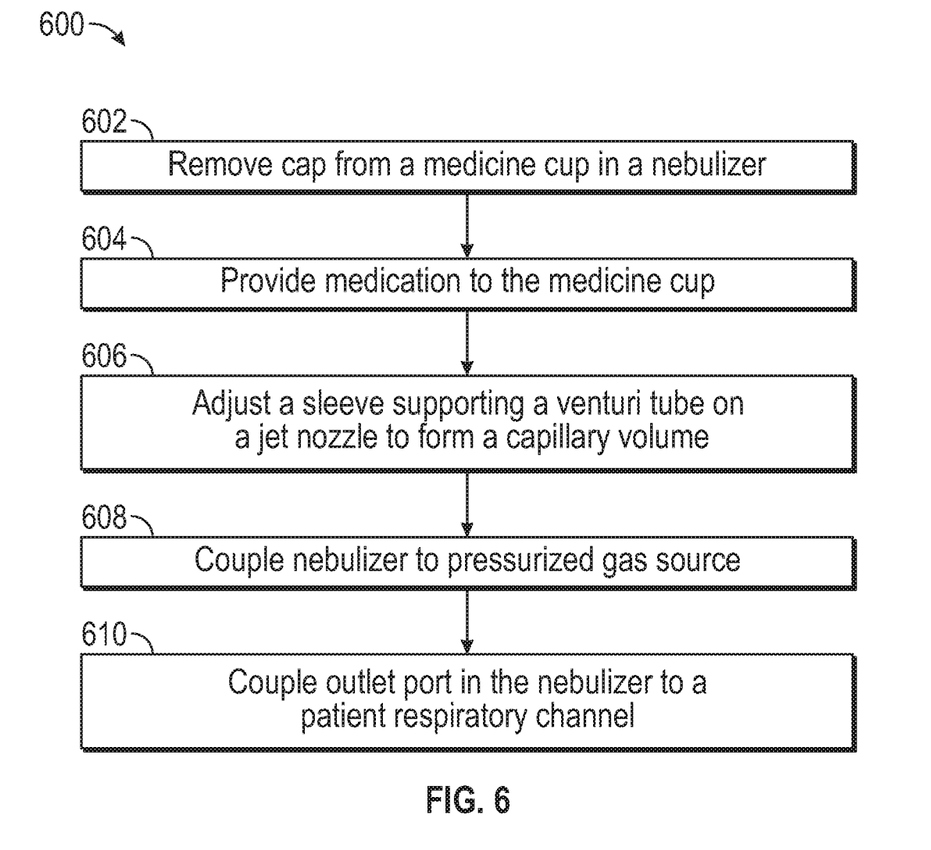
FIG. 6 illustrates a flowchart in a method for providing a medicine to a patient, according to some embodiments.

Method 500 may be performed in the context of a high volume production of inexpensive, disposable assemblies for breath-actuated nebulizers. In some embodiments the assemblies are rigid and have no flexible parts and no moving parts, which may make the assemblies more rugged and durable. Each or at least one of the forming steps 502 through 506 in method 500 may include at least one of injection molding or three-dimensional (3D) printing of the parts and components described in the steps.

FIG. 6 illustrates a flowchart in a method 600 for providing a medicine to a patient, according to some embodiments. In some embodiments, steps in method 600 may be performed at least partially by healthcare personnel at a healthcare facility. In some embodiments, steps in method 600 may be performed at least partially by a user performing a self-medication procedure, or providing medication to another person. Steps in FIG. 6 may be performed at least partially by an automated machine having a computer including a memory circuit and a processor circuit. The memory circuit may store commands which, when executed by the processor circuit, cause the machine to perform the steps in method 600. Steps in methods consistent with method 600 may be performed in any order, and the sequence illustrated in FIG. 6 is not limiting of embodiments consistent with the scope of the present disclosure. Further, some steps in method 600 may be performed overlapping in time. Moreover, some steps in method 600 may be performed simultaneously, or quasi-simultaneously, without departing from the scope of the present disclosure. Methods consistent with the present disclosure may include at least one, but not all of the steps in method 600.

Method 600 may be performed in connection with a breath-actuated nebulizer having an outlet port protruding from a cap that fits onto a medicine cup. The medicine cup may include an upper chamber and a lower chamber, the lower chamber including a pressurized gas port (e.g., breath-actuated nebulizer 100, outlet port 111, cap 110, medicine cup 135, upper chamber 120, lower chamber 130 and pressurized gas port 133, cf. FIG. 1). The breath-actuated nebulizer in method 600 may be coupled to a pressurized gas source such as a liquefied gas canister or a wall pipeline in a healthcare facility, the wall pipeline having a wall outlet (e.g., healthcare facility 300, canister 310, wall pipeline 320 and wall outlet 321, cf. FIG. 3).

Step 602 includes removing the cap from the medicine cup in the nebulizer. In some embodiments, step 602 includes pressing the cap to snap it apart from the medicine cup. In some embodiments, step 602 may include twisting the cap by a quarter turn or a partial turn around the medicine cup to disengage a tongue link. Step 604 includes providing medicine to the medicine cup. Step 606 includes adjusting a sleeve supporting a venturi tube on a jet nozzle (e.g., venturi tube 101, cf. FIG. 1). The jet nozzle may be configured to provide a pressurized gas flow through a nozzle tip. Step 606 may include forming a capillary volume between the jet nozzle and the sleeve (e.g., capillary volume 121, cf. FIG. 1). Accordingly, step 606 may include carefully positioning the nozzle tip in the proximity of a diverter formed on a rib in the sleeve. Step 608 includes coupling the nebulizer to the pressurized gas source. In some embodiments, step 608 includes coupling the nebulizer to the wall pipeline containing a pressurized gas flow and turning on the wall outlet of the wall pipeline. In some embodiments, step 608 includes coupling the nebulizer to the liquefied gas canister. Step 608 may include inserting the pressurized gas port in the lower chamber of the medicine cup to an outlet fixture of the pressurized gas source. Step 610 includes coupling the outlet port in the nebulizer to a patient's respiratory channel or an artificial airway.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A breath-actuated nebulizer for delivering medicine, comprising:
    a medicine cup configured to hold the medicine and comprising (i) a first gas inlet configured to permit ambient gas into the medicine cup, (ii) a second gas inlet configured to conduct pressurized gas into the medicine cup, and (iii) an outlet that is configured to direct a combination of the ambient gas, the medicine, and the pressurized gas out of the medicine cup;
    a jet nozzle, in fluid communication with the second gas inlet, comprising a jet orifice configured to produce a jet stream of the pressurized gas;
    a sleeve coupled to the jet nozzle and defining a pressure passage;
    a venturi tube comprising an inlet opening, an outlet opening, and a venturi passage therebetween, and a throat, wherein a cross-sectional area of the venturi passage decreases from the inlet opening to the throat, and increases from the throat toward the outlet opening, and a first hole is positioned at the throat such that the pressure passage is in fluid communication with the first gas inlet and the medicine cup through the first hole; and
    a capillary volume defined between the jet nozzle and the sleeve;
    wherein, without moving parts of the nebulizer, the pressure passage changes from a first high pressure, when the ambient gas is not drawn into the medicine cup through the venturi tube such that the medicine is not conducted from the medicine cup through a portion of the pressure passage to the capillary volume, to a second low pressure, when the ambient gas is drawn into the medicine cup through the venturi tube such that the medicine is conducted from the medicine cup toward the jet stream by moving through the portion of the pressure passage to the capillary volume.

2. The nebulizer of claim 1, further comprising a diverter that is configured to transition the jet stream from an axial orientation within the medicine cup to a radial orientation.

3. The nebulizer of claim 1, wherein the capillary volume forms a gap around the jet orifice.

4. The nebulizer of claim 3, wherein the jet stream, upon exiting the jet orifice, is diverted into a radial orientation, such that the jet stream impinges upon the medicine drawn up from the capillary volume.

5. The nebulizer of claim 1, wherein the pressure passage comprises a first portion that is in fluid communication with the throat of the venturi tube and extends-from the venturi tube toward the jet stream, and the pressure passage further comprises a second portion being in fluid communication with the medicine cup to draw the medicine through the second portion of the pressure passage toward the jet stream.

6. The nebulizer of claim 5, wherein the outlet comprises an outlet port, and the ambient gas is drawn into the medicine cup through the venturi tube when the combination of the ambient gas, the medicine, and the pressurized gas is evacuated from the medicine cup through the outlet port.

7. The nebulizer of claim 3, further comprising hermetically sealing the capillary volume in the medicine cup, except for the gap around the jet orifice.

8. A method, comprising:
providing a breath-actuated nebulizer for delivering medicine, comprising:
- a medicine cup configured to hold the medicine and comprising (i) a first gas inlet configured to permit ambient gas into the medicine cup, (ii) a second gas inlet configured to conduct pressurized gas into the medicine cup, and (iii) an outlet that is configured to direct a combination of the ambient gas, the medicine, and the pressurized gas out of the medicine cup;
- a jet nozzle, in fluid communication with the second gas inlet, comprising a jet orifice configured to produce a jet stream of the pressurized gas;
- a sleeve coupled to the jet nozzle and defining a pressure passage;
- a venturi tube comprising an inlet opening, an outlet opening, and a venturi passage therebetween, and a throat, wherein a cross-sectional area of the venturi passage decreases from the inlet opening to the throat, and increases from the throat toward the outlet opening, and a first hole is positioned at the throat such that the pressure passage is in fluid communication with the first gas inlet and the medicine cup through the first hole; and
- a capillary volume defined between the jet nozzle and the sleeve;
- wherein, without moving parts of the nebulizer, the pressure passage changes from a first high pressure, when the ambient gas is not drawn into the medicine cup through the venturi tube such that the medicine is not conducted from the medicine cup through a portion of the pressure passage to the capillary volume, to a second low pressure, when the ambient gas is drawn into the medicine cup through the venturi tube such that the medicine is conducted from the medicine cup toward the jet stream by moving through the portion of the pressure passage to the capillary volume;

removing a cap from the medicine cup;

providing medicine to the medicine cup;

placing the cap back on the medicine cup; and coupling the nebulizer to a pressurized gas source such that a jet stream is created by the jet orifice of the nebulizer, wherein an entirety of a pressurized gas from the pressurized gas source is directed to the jet orifice.

9. The method of claim 8, wherein coupling the nebulizer to the pressurized gas source comprises coupling the nebulizer to a wall source containing a pressurized gas flow.

10. The method of claim 8, wherein coupling the nebulizer to the pressurized gas source comprises coupling the nebulizer to a liquefied gas canister.

11. The method of claim 8, wherein the pressure passage changes to the second low pressure by a respiration event.

* * * * *